(12) United States Patent
Derouet

(10) Patent No.: US 8,114,140 B2
(45) Date of Patent: Feb. 14, 2012

(54) IMPLANTABLE ORTHOPAEDIC DEVICE COMPOSED OF A SUPPORT STRUCTURE HAVING AT LEAST ONE ORIFICE ASSOCIATED WITH A NUT, FOR THE PASSAGE OF A LOCKING SCREW

(75) Inventor: Guillaume Derouet, Saint-Herblain (FR)

(73) Assignee: D.L.P. (FR)

( * ) Notice: Subject to any disclaimer, the term of this patent is extended or adjusted under 35 U.S.C. 154(b) by 300 days.

(21) Appl. No.: 12/445,022

(22) PCT Filed: Apr. 17, 2008

(86) PCT No.: PCT/FR2008/050688
§ 371 (c)(1),
(2), (4) Date: Apr. 9, 2009

(87) PCT Pub. No.: WO2008/145902
PCT Pub. Date: Dec. 4, 2008

(65) Prior Publication Data
US 2010/0174324 A1 Jul. 8, 2010

(30) Foreign Application Priority Data
Apr. 17, 2007 (FR) ..................... 07 02777

(51) Int. Cl.
*A61B 17/86* (2006.01)
(52) U.S. Cl. ..................................... 606/305
(58) Field of Classification Search ........... 606/267, 606/286–292, 305–308
See application file for complete search history.

(56) References Cited

U.S. PATENT DOCUMENTS

| 6,454,769 | B2 * | 9/2002 | Wagner et al. | 606/279 |
|---|---|---|---|---|
| 7,195,633 | B2 | 3/2007 | Medoff et al. | |
| 7,572,279 | B2 * | 8/2009 | Jackson | 606/266 |
| 7,686,837 | B2 * | 3/2010 | Gasser et al. | 606/287 |
| 7,846,163 | B2 * | 12/2010 | Fourcault et al. | 606/68 |
| 2004/0267261 | A1 * | 12/2004 | Derouet | 606/70 |
| 2005/0154392 | A1 * | 7/2005 | Medoff et al. | 606/69 |
| 2006/0235399 | A1 * | 10/2006 | Carls et al. | 606/69 |

FOREIGN PATENT DOCUMENTS

| EP | 0988833 | 3/2000 |
|---|---|---|
| EP | 1488754 | 12/2004 |
| FR | 2792185 | 10/2000 |
| FR | 2867962 | 9/2005 |
| FR | 2915081 | 10/2008 |
| WO | WO0115612 | 3/2001 |
| WO | WO03043513 | 5/2003 |

* cited by examiner

*Primary Examiner* — Thomas C. Barrett
*Assistant Examiner* — Michael Araj
(74) *Attorney, Agent, or Firm* — McHale & Slavin, P.A.

(57) ABSTRACT

The device includes a support structure (2) having an orifice (3) that delimits a seat (5) for receiving a nut (6) intended to cooperate with a locking screw (4). The seat (5) comprises an upper part (5a) and a lower part (5b), both shaped as truncated spheres and concentric to each other. Furthermore, the nut (6) has a spherical contour (11), and the screw head (15) has a lower part (15b), also with a spherical contour, and an upper part (15a) provided with a thread (17). The upper (15a) and lower (15b) parts of the screw head (15) cooperate respectively with the complementary thread (14) of the nut (6) and with the lower part (5b) of the receiving seat (5) such that, in the final phase of screwing the spherical contour (11) of the nut (6) bears against the upper spherical part (5a) of the seat (5), and of the lower part of the screw head (15b) against the lower spherical part (5b) of the seat (5).

9 Claims, 3 Drawing Sheets

IMPLANTABLE ORTHOPAEDIC DEVICE COMPOSED OF A SUPPORT STRUCTURE HAVING AT LEAST ONE ORIFICE ASSOCIATED WITH A NUT, FOR THE PASSAGE OF A LOCKING SCREW

CROSS REFERENCE TO RELATED APPLICATIONS

This is a national stage filing in accordance with 35 U.S.C. §371 of PCT/FR2008/050688, filed Apr. 17, 2008, which claims the benefit of the priority of French Patent Application No. 0702777, filed Apr. 17, 2007.

FIELD OF INVENTION

The present invention relates to a new orthopedic implant system of the type having a support structure provided with at least one orifice associated with a nut, for the passage of a fixing screw intended to fasten into the receiving bone material.

Most orthopedic implants, in particular osteosynthesis implants, comprise a support structure, often of the plate type, in which are arranged several orifices provided for the passage of a fixing screw able to anchor into the receiving bone material. The general form and dimensions of the support plate are adapted to the implantation constraints.

Some implants are distinguishable by the presence of means providing the fixing screw with a possibility of angular orientation relative to the axis of its receiving orifice; they enable the practitioner to position at best the screw within the receiving bone material, in particular according to the implantation site and to the encountered spatial constraints.

Particularly interesting implants of this type are described in WO-A-03/043513. Those orthopedic implants are of the type having a support structure provided with at least one orifice for the passage of a fixing screw, and whose contours delimit a receiving housing for a nut provided with an internal thread intended to cooperate with a mating thread arranged on the screw head.

The nut is locked in rotation within its receiving housing, so as to prevent its rotation around its axis (corresponding to the axis of its thread). The nut has at least one freedom degree within the housing, according to a predetermined acceptable tilting domain, which enables a tilting of its axis relative to the axis of the receiving housing, so as to enable a self-centering of the screw and the associated nut whatever the admissible orientation of the axis of the screw relative to the axis of the associated orifice.

In this type of implant, the head of the screw is intended to rest on a side of the support and the nut is intended to rest on the other side of this support, in such a way to make it possible for the support structure to be tightened between these two elements at the end of the tightening of the screw body into the receiving bone material.

In practice, the corresponding implants have good stay-on and locking qualities, while providing an interesting possibility of spatial orientation of the fixing screws relative to the axis of their receiving orifices.

Starting from such an implant, the applicant has developed a new simple and practical structure, also having good locking and stay-on qualities, while enabling a certain possibility of spatial orientation of the fixing screws within their receiving orifices. Implants objects to the present invention are also interesting in that they can be very compact and have a reduced thickness dimension.

SUMMARY OF THE INVENTION

For this purpose, the orthopedic device according to the invention is of the type comprising:
- a support structure delimited by an upper face and a lower face, the latter being intended to come opposite to the receiving bone material, said support structure being provided with at least one housing and at least one orifice passing through said housing, said housing and said orifice having the same axis,
- at least one nut provided with an internal thread, said nut being shaped so as to be caught within one of said housings, and
- at least one fixing screw consisting of a screw head and a screw body, said screw head being provided with a thread able to cooperate with said nut thread, and said screw body being provided with a thread able to cooperate with the receiving bone material, said nut being locked in rotation within said receiving housing so as to be prevented from rotating around its axis, and said nut having at least one freedom degree within said receiving housing, according to a predetermined acceptable tilting domain, so as to enable a tilting of its axis relative to the axis of the receiving housing, said fixing screw being intended to be screwed within one of said orifices and the associated nut thereof, according to a selected angle in the acceptable tilting domain.

According to the invention, the nut receiving housing comprises an upper part located on the upper face side of the support structure and a lower part located on the lower face side of said support structure, both parts being generally truncated sphere shaped and concentric to each other. Further, the nut has a truncated sphere shaped peripheral contour mating with the truncated sphere shaped upper part of the receiving housing, and the screw head comprises an upper part provided with the aforementioned thread and a lower part whose contour has a generally truncated sphere shape, mating with the truncated sphere shaped lower part of the receiving housing.

The upper and lower parts of the screw head are intended to cooperate, during the final screwing step of the screw, with the mating thread of the nut and the lower part of the receiving housing, respectively, so as to tend to separate said nut from the lower part of the receiving housing, which lead to the locking of the screw by the continuation of screwing, in the result of a forced rest of the peripheral contour of the nut against the mating upper part of the receiving housing, and, in the same time, of a forced rest of the lower part of the screw head against the mating lower part of the housing.

According another feature, truncated sphere shaped lower and/or upper parts of the nut receiving housing are constituted by the central surface of an add-on clip intended to partially close said housing. Using such add-on clips particularly aims at helping the setting of nuts within their receiving housings (but also their possible unsetting), while ensuring an efficient stay-on of these nuts. This kind of clip is advantageously in the form of an open ring, comprising a snapping rib able to fit within a suitably shaped groove arranged in the nut fitting housing.

According to a preferred embodiment, truncated sphere shaped upper and lower parts of the nut receiving housing are constituted by a surface integral with the support structure and by the central surface of an add-on clip, respectively. Such a structure makes it possible to use the bone material as a resting surface ensuring an optimal stay-on of the clip on the support structure.

According to other features which can be taken in combination or individually:

overall dimensions of the screw head correspond to the diameter of the nut central orifice, these dimensions of the screw head being yet smaller than those of the upper part of the receiving housing;

the height of the screw head, between its free end and the lower end of its truncated sphere shaped lower part, is lower or equal to the height of the associated through-orifice; each of these structural features helps to optimize the compact shape of the device, and in particular contributes to limit the space occupied by the screw head, the latter being able to be totally embedded in the thickness of the support structure;

the nut receiving housing comprises a truncated sphere shaped upper part whose radius is greater than that of truncated sphere shaped lower part;

the means for locking the nut in rotation within its receiving housing, are comprised by at least one embossment arranged in one of said pieces and cooperating with an adapted recess arranged in the other one of said pieces;

the external diameter of the screw body thread is smaller than the external diameter of the head thread, and this head thread consists of n screw threads, n being higher or equal to 2, which are shifted by 1/n turn and whose pitch corresponds to that of the nut thread and to that of said screw body thread. The plurality of threads makes it possible to optimize the tightening characteristics of the screw head into the nut.

The present invention also relates to the support structure provided with one or more nuts, for an implantable orthopedic device as above described.

The invention will be more fully described, without any limitation, by the following description of a particular embodiment, given only by way of example and illustrated on the following drawings.

DETAILED DESCRIPTION OF THE INVENTION

Figure 1:
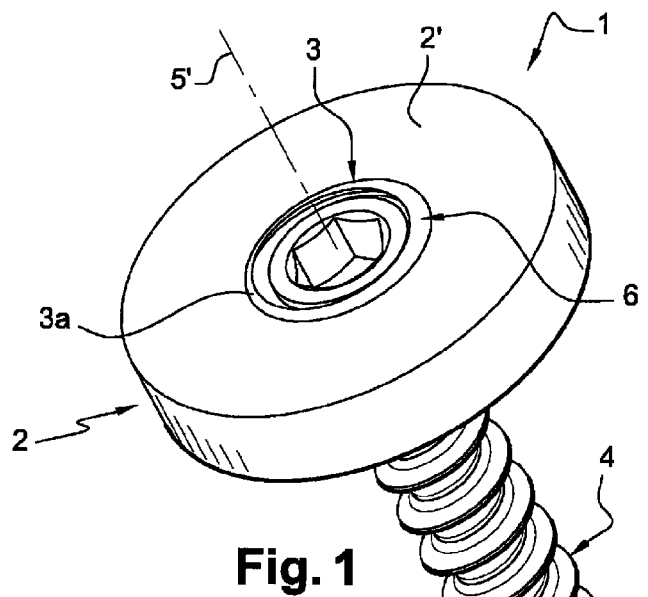
FIG. 1 is a general view of an implantable orthopedic device according to the invention, in a perspective view from its upper surface, and in which the fixing screw is suitably fitted through a receiving orifice of a schematically shown support plate.
Figure 2:
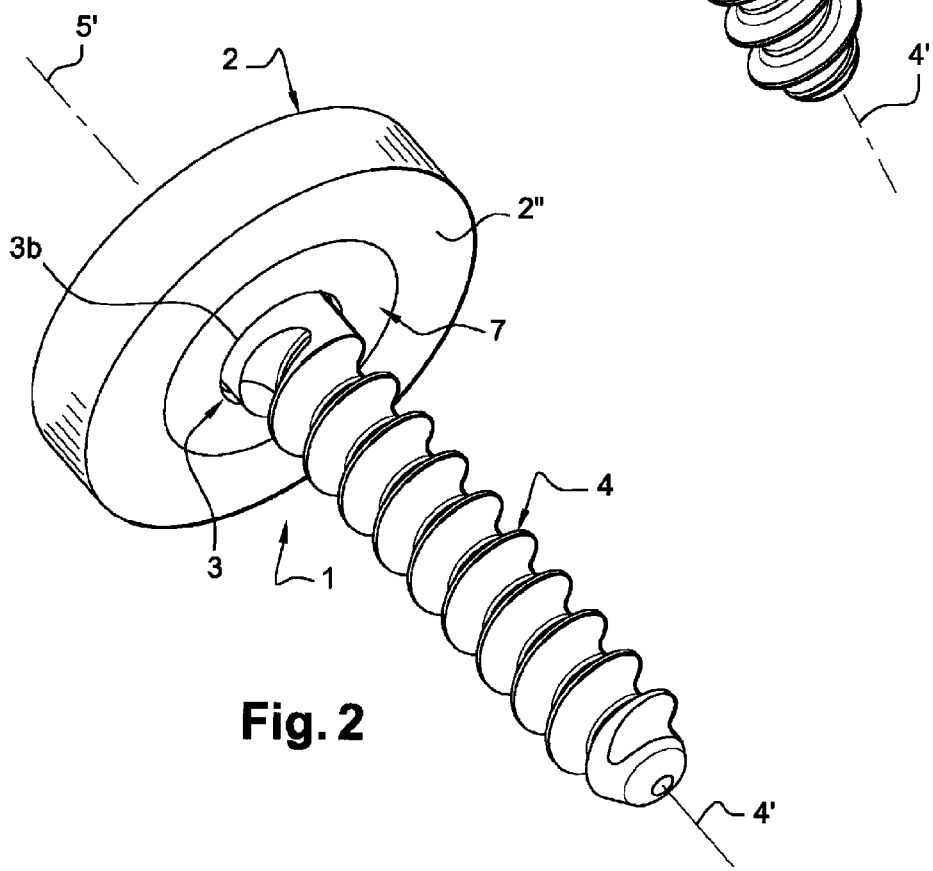
FIG. 2 is another general view of the orthopedic device of FIG. 1, in a perspective view from the lower face of its support plate (intended to rest against the surface of the receiving bone material)

The implantable orthopedic device 1, shown in a perspective view in FIGS. 1 and 2, essentially comprises a support structure 2 (schematically shown herein), in which is arranged a circular through-orifice 3 receiving a fixing screw 4. This support structure 2 is for example comprised by a 2 to 3 mm thickness plate delimited by an upper face 2' and a lower face 2". The screw 4 is intended to be inserted into the orifice 3 on the upper face 2' side, and to go out of it by the lower face 2", the latter being intended to rest against the receiving bone material (not shown).

Generally, the support plate 2 can comprise several through-orifices 3 suitably arranged one relative to the other. This type of orthopedic implant is particularly intended to be positioned in a fractured bone (not shown), for example a radius epiphysis.

Figure 3:
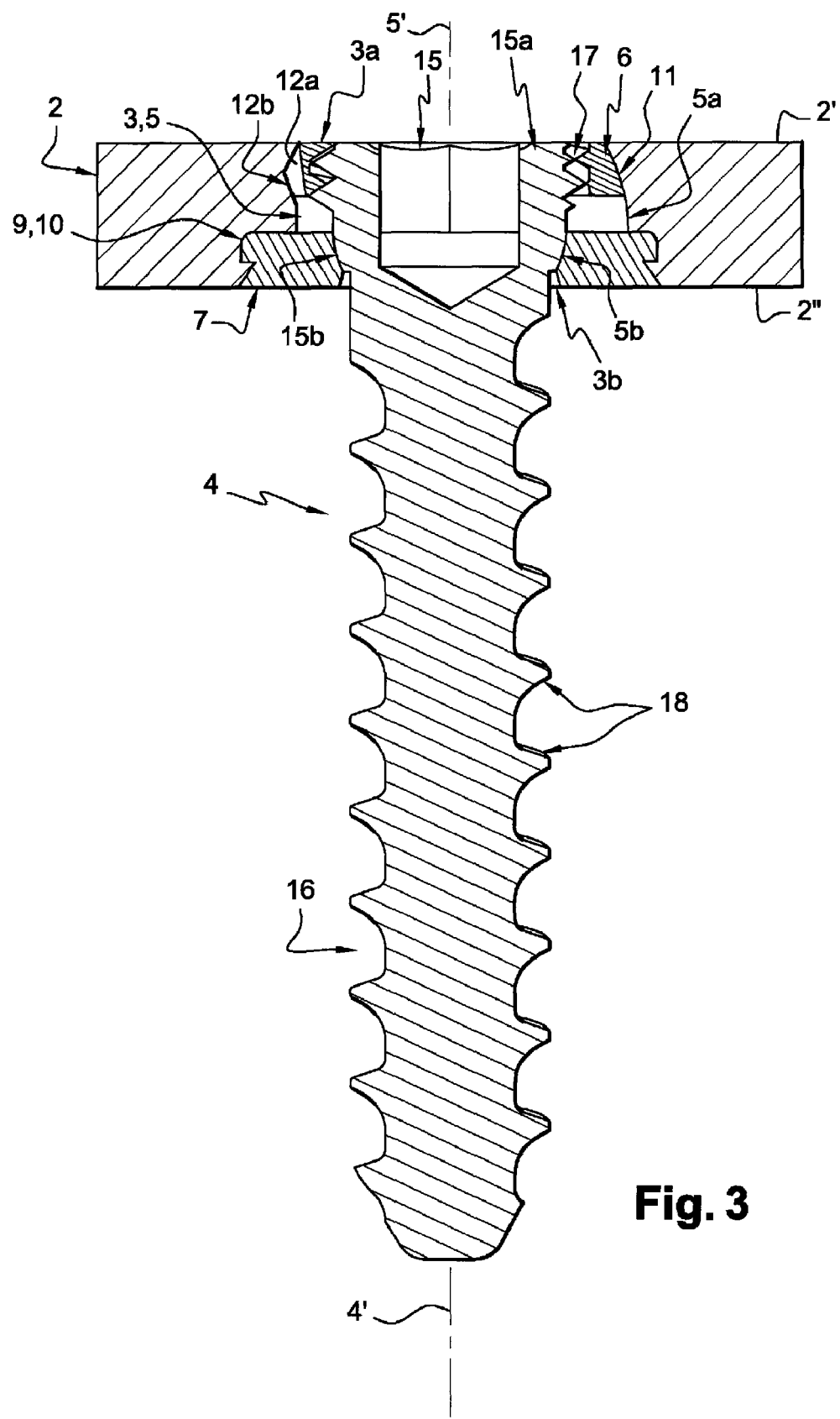
FIG. 3 show the orthopedic device according to FIGS. 1 and 2, in a cross section passing through the axis of the support plate through-orifice.
Figure 4:
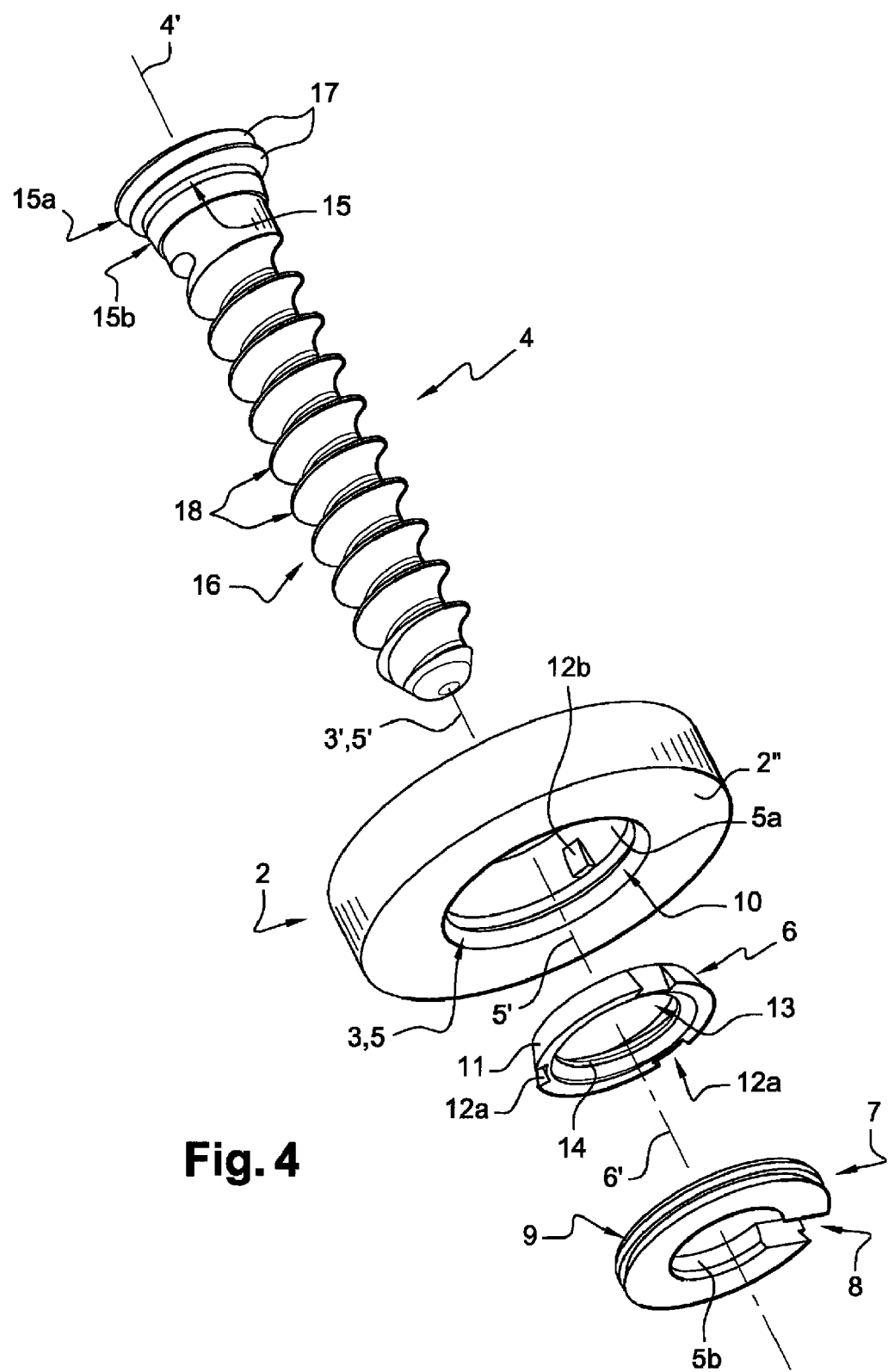
FIG. 4 is an exploded perspective view of the orthopedic device according to FIGS. 1 to 3, showing in details the different components thereof.

It can be seen in FIGS. 3 and 4 that the through-orifice 3 extends through a housing 5 in which a nut 6 able to cooperate with a mating thread of the fixing screw 4 is positioned and caught. The nut 6 comprises a certain freedom degree within its receiving housing 5, according to a predetermined acceptable tilting domain, so as to provide an efficient locking of the fixing screw 4 at the end of the screwing into the receiving bone material, whatever the admissible orientation of the axis 4' thereof relative to the axis 5' of the associated through-orifice 3. Further, this nut 6 is locked in rotation within its receiving housing 5 so as to be prevented from rotating around its axis 6'.

The central wall of the through-orifice 3 delimits the above mentioned receiving housing 5. The through-orifice 3 and the housing 5 have the same axis 5'.

The receiving housing 5 of the nut 6 is particularly delimited at the upper part thereof (i.e. on the surface 2' side of the support 2) by a surface 5a having a generally truncated sphere shape and at the lower part thereof by a surface 5b also having a truncated sphere shape (this surface 5b being intended to position on the receiving bone material side). Surfaces 5a and 5b are concentric; they are centered at a point located on the axis 5' of the orifice 3, within the thickness of the support 2. The upper part 5a has a radius greater than that of the lower part 5b; also, the diameter of the upper through-edge 3a of the through-orifice 3 is greater than that of the lower through-edge 3b thereof.

More precisely, the upper part 5a of the housing 5 is obtained by a suitable working of the support structure 2; this upper part 5a is then integral with the support structure 2 so that the resistance thereof to thrust forces is optimized.

The lower part 5b of the housing 5 is formed by the central surface of an add-on clip 7 shown in details in FIG. 4. This clip 7, once suitably add-on, enables the locking of the nut 6 within its receiving housing 5. Said clip 7 is in the form of an opened circular ring provided with a slot 8 providing thereof a certain radial elasticity in order it to be embedded within the support structure 2. On its external periphery, this clip 7 is provided with a peripheral rib or embossment 9 able to embed in a circular groove 10 suitably arranged within the receiving housing 5.

The nut 6, being in the form of a complete ring, comprises a generally truncated sphere shaped peripheral surface or contour 11 which mates with to upper part 5a of the receiving housing 5. This peripheral surface 11 is provided with cavities or recesses 12a (which are three here) within which fit mating embossments 12b forming kinds of tenons arranged on the upper part 5a of the housing 5. The cooperation between these elements 12a and 12b ensure that the nut 6, once suitably positioned in its receiving housing 5, will be locked in rotation around its axis 6'; these tenons 12b and recesses 12a are structured to enable a certain mobility of the nut 6 within the housing 5, and in particular to enable a certain tilting of the axis 6' thereof relative to axis 5' of the housing 5, in a predetermined acceptable domain. The central orifice 13 of the nut 6 is provided with a thread 14 (extending around the symmetry axis 6').

As for the screw 4, it comprises a screw head 15 and a screw body 16.

The screw head 15 comprises a, upper part 15a provided with a thread 17 intended to engage with the mating thread 14 of the nut 6 at the end of the screwing of the screw 6. This screw head 15 also comprises a lower part 15b whose contour has a generally truncated sphere shape mating with the lower part 5b of the receiving housing 5.

As for the screw body 16, it comprises a thread 18 that extends all over the length thereof and that is shaped to cooperate with the receiving bone material.

Structural and dimensional characteristics of this screw body 16 having the thread 18 are adapted to make possible for it to pass through the threaded orifice 13 of the nut 6, and, more generally, through the orifice 3 of the support plate 2. In particular, the external diameter of the thread 18 is provided smaller than the external diameter of the thread 17 of the screw head 15, and also smaller than the diameter of the through-opening 3b of the orifice 3.

Moreover, the head thread 17 consists of 2 screw threads which are shifted by ½ turn and whose pitch is the same as that of the thread 14 of the nut 6 and that of body thread 18.

The screw head 15 is so shaped to totally fit within the thickness of the support structure 2, in such a way non to project beyond the upper face 2' at the end of the screwing, as shown in FIG. 1. For this purpose, the height of the screw head 15, i.e. the distance between the free end of its upper part 15a and the lower end of its lower part 15b, is lower or equal to the height of the through-orifice 3.

In practice, firstly, a nut 6 is suitably positioned within each of the receiving housings 5 of the support structure 2, in order that the peripheral surface 11 thereof comes opposite to the upper part 5a of said receiving housing 5 and that the recesses 12a thereof accommodate one of the mating tenons 12b. Next, these nuts 6 are caught within their respective receiving housings 5 by the fitting of the closing clips 7.

This support structure 2, provided with nuts 6, is then able to be implanted by the practitioner in order to treat for example a fracture of a patient. For this purpose, he can firstly use a drilling bush, before the fitting of screws, to initiate positioning holes within the bone material, through the orifices 3.

Next, the practitioner can introduce and screw a fixing screw 4 through each of the through-orifices 3, with the adapted tilting relative to the axis of said orifice 3 (in the limits of the acceptable tilting domain). This tilting possibility is particularly related to the fact that the nut 6 has a freedom degree in its receiving housing 5, said nut coming then "automatically" in alignment with the fixing screw 4. The angular adjustment of the screw 4 is possible within a conical volume having an apex angle preferably included between 20° and 30°, the axis thereof being merged with the axis 5' of the through-orifice 3.

The practitioner continues to screw the screw 4 until the screw head 15 enter within the orifice 3/housing 5 assembly (FIGS. 1 to 3). Then, as can be seen in FIG. 3, the thread 17 of the screw head 15 comes to cooperate with the mating thread 14 of the nut 6. At the end of screwing, the lower part 15b of the screw head 15 comes to rest on the mating surface of the lower part 5b of the receiving housing 5 (it should be noted that the resting of the support structure 2 on the receiving bone material helps the clip 7 to stay-on); and that particular cooperation tends to separate the nut 6 from the lower part 5a of the housing 5. This separation phenomenon leads the nut contour 11 to come into forced rest against the mating upper part 5a of the housing 5; the lower part 15b of the screw head 15 also comes into a forced rest against the mating lower part 5b of the housing 5.

This double forced rest "in separation direction", or "in expansion direction", makes it possible for the screw 4 to be locked through its receiving orifice 3; the strength of the locking is notably function of the screwing force applied by the practitioner during this final screwing step. In this final configuration, the contact of the truncated sphere shaped surfaces 5a and 5b of the receiving housing 5 with the mating surfaces 11 and 15b of the nut 6 and of the screw head 15, simultaneously, enables obtaining an efficient and quality tightening, whatever the tilting of the axis 4' of the screw 4 and of the axis 6' of the nut 6 relative to the axis 5' of the orifice 3/housing 5 assembly (in the acceptable tilting domain).

In this final configuration, the screw head 15 is totally embedded in the thickness of the support structure 2, without any particular protrusion beyond the upper surface 2' of the support 2.

According to the needs, the practitioner will just have to exert a sufficient unscrewing force to provide the unscrewing of the screws in order to completely remove them from the receiving bone material.

Generally, this particular implantable orthopedic device structure is interesting in that it enables obtaining an efficient locking of the screw within the orifice/receiving housing assembly. Further, this type of structure is interesting in that it is particularly compact and is able to embody support plates whose thickness is limited to a few millimeters (in the order of 2 to 3 mm thick).

The invention claimed is:

1. Implantable orthopedic device comprising:
    a support structure (2) delimited by an upper face (2') and a lower face (2"), said lower face adapted to rest against a receiving bone material, said support structure (2) being provided with at least one housing (5) and at least one orifice (3) passing through said housing (5), said housing (5) and said orifice (3) having the same axis (5'),
    at least one nut (6) provided with an internal thread (14), said nut (6) being shaped so as to be caught within one of said housings (5), and
    at least one fixing screw (4) consisting of a screw head (15) and a screw body (16), said screw head (15) being provided with a thread (17) configured to cooperate with said nut thread (14), and said screw body (16) being provided with a thread (18) configured to cooperate with the receiving bone material, said nut (6) being locked against rotation within said receiving housing (5) so as to prevent said nut from rotating around its axis (6'), and said nut (6) having at least one degree of freedom within said receiving housing (5), according to a predetermined acceptable tilting domain, so as to enable a tilting of its axis (6') relative to the axis (5') of said receiving housing (5), said fixing screw (4) being intended to be screwed within one of said orifices (3) and the associated nut (6) thereof, according to a selected angle in the acceptable tilting domain, said housing (5) further comprising an upper part (5a) located on the upper face (2') side of the support structure (2) and a lower part (5b) located on the lower face (2") side of said support structure (2), both parts being generally truncated sphere shaped and concentric to each other, and said nut (6) having a truncated sphere shaped peripheral contour (11) mating with said truncated sphere shaped upper part (5a) of the receiving housing (5), said screw head (15) having an upper part (15a) provided with said thread (17) and a lower part (15b) whose contour has a generally truncated sphere shape mating with said truncated sphere shaped lower part (5b) of the receiving housing (5), said upper (15a) and lower (15b) parts of said screw head (15) configured to cooperate, during the final screwing step of said screw (4), with the thread (14) of said nut (6) through the mating thread (17) thereof and with said lower part (5b) of the receiving housing (5), respectively, so as to tend to separate said nut (6) from said lower part (5*b*) of the receiving housing (5), and then impart a forced rest of the peripheral contour (11) of said nut (6) against said mating upper part (5*a*) of the receiving housing (5) and a forced rest of the lower part (15*b*) of said screw head (15) against said mating lower part (5*b*) of the receiving housing (5), in order to obtain the locking of said screw (4) during the final screwing step.

2. Implantable device according to claim 1, wherein the truncated sphere shaped upper (5*a*) and/or lower (5*b*) parts of the housing (5) are constituted by the central surface of an add-on clip (7) intended to partially close said receiving housing (5) and ensure the retention of the nut (6).

3. Implantable device according to claim 2, wherein the truncated sphere shaped upper (5*a*) and lower (5*b*) parts of the receiving housing (5) of the nut (6) are constituted by a surface integral with the support structure (2) and by the central surface of the add-on clip (7), respectively.

4. Implantable device according to 2, wherein the clip (7) for the stay-on of the nut (6) is in the general form of an open ring, said ring (7) including a snapping rib (9) configured to cooperate with a suitably shaped groove (10) arranged in the receiving housing (5).

5. Implantable device according to claim 1, wherein the overall dimensions of the screw head (15) correspond to the diameter of the central surface (13) of the nut (6), said dimensions of the screw head (15) being yet smaller than those of the upper part (5*a*) of the receiving housing (5).

6. Implantable device according to claim 1, wherein the height of the screw head (15), between its free end and the lower end of its truncated sphere shaped lower part (15*b*), is lower or equal to the height of the associated through-orifice (3).

7. Implantable device according to claim 1, wherein the receiving housing (5) of the nut (6) comprises a truncated sphere shaped upper part (5*a*) whose radius is greater than that of truncated sphere shaped lower part (5*b*).

8. Implantable device according to claim 1, wherein the device includes at least one embossment (12*b*) and a mating recess (12*a*), one being arranged at the receiving housing (5) and the other being arranged at the peripheral contour (11) of the nut (6), said embossment (12*b*) and said recess (12*a*) being positioned and shaped so as to form the means for locking the nut (6) against rotation within its receiving housing (5).

9. Implantable device according to claim 1, wherein the external diameter of the body thread (18) of the screw (4) has an external diameter that is smaller than the external diameter of the head thread (17) of said screw (4), and in that said head thread (17) consists of n threads, n being higher or equal to 2, which are shifted by 1/n turn and whose pitch corresponds to that of the thread (14) of the nut (6) and to that of said body thread (18).

* * * * *